Figure 1:
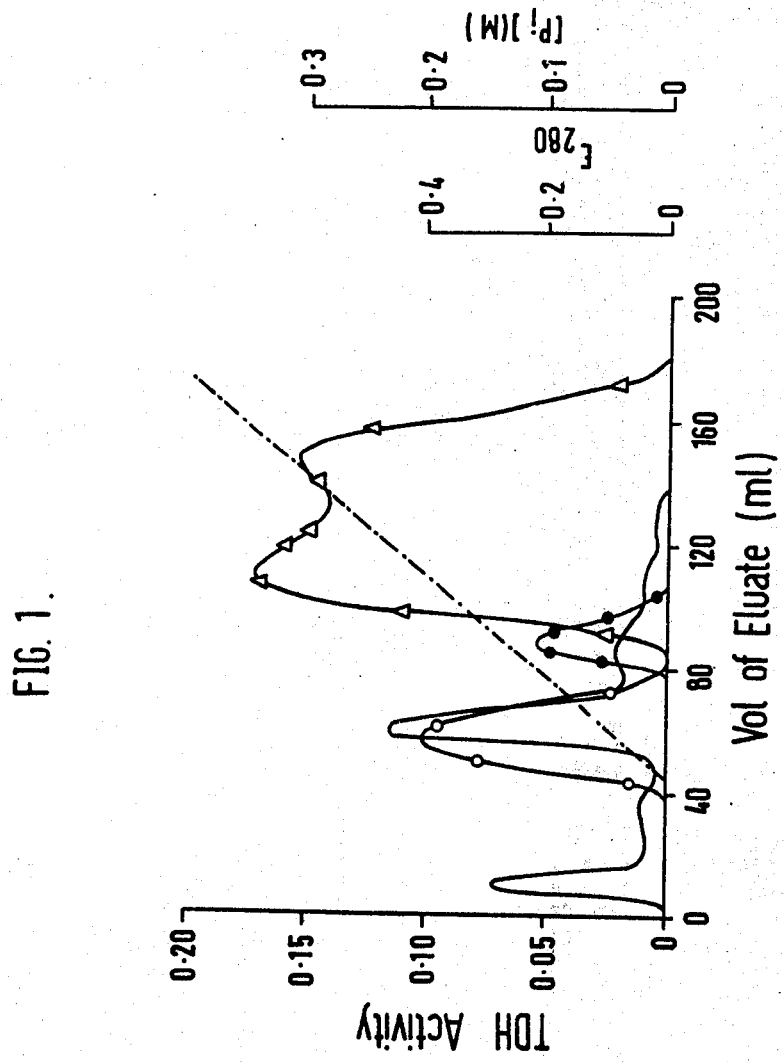

United States Patent [19]

Dean et al.

[11] 3,985,690

[45] Oct. 12, 1976

[54] ENZYME SEPARATION

[76] Inventors: Peter Duncan Goodearl Dean, 43 Redgate, Formby, Lancashire; Christopher Robin Lowe, Fairlight, 238 Windsor Road, Maidenhead, Berkshire, both of England

[22] Filed: May 13, 1974

[21] Appl. No.: 469,221

Related U.S. Application Data

[63] Continuation of Ser. No. 224,528, Feb. 8, 1972, abandoned.

[30] Foreign Application Priority Data

Feb. 11, 1971 United Kingdom............... 4469/71

[52] U.S. Cl.................................... 260/6; 260/7.5; 260/8; 260/17.4 R; 260/17.4 GC; 260/17.4 UC; 260/75 T; 260/112 R; 536/22; 536/45; 536/58; 526/7; 526/23; 526/21

[51] Int. Cl.²........................................ C08L 89/00

[58] Field of Search............... 260/17.4 R, 233.3 R, 260/233.3 A, 233.5, 209 D, 211.5 R, 234 R, 89.7 S, 75 T, 112 R, 91.3 VA, 93.5 R, 6, 7.5, 8, 17.4 GC, 17.4 UC

[56] References Cited

FOREIGN PATENTS OR APPLICATIONS 1,959,169  6/1970  Germany
   55,906 11/1968  United Kingdom Primary Examiner—Melvyn I. Marquis
Attorney, Agent, or Firm—Johnston, Keil, Thompson & Shurtleff

[57] ABSTRACT

A reactive matrix comprises a co-enzyme chemically attached to a water insoluble organic polymeric support material. The reactive matrix may be used in a process for the separation of mixtures containing a plurality of enzymes.

8 Claims, 6 Drawing Figures

ε-Amino-caproyl - NAD - Sepharose

ENZYME SEPARATION

This is a continuation of application Ser. No. 224,528, filed Feb. 8, 1972 and now abandoned.

This invention relates to the separation of mixtures containing a plurality of enzymes.

In the separation and purification of crude mixtures containing enzymes together with other organic materials, it has been proposed to use the technique of affinity chromatography, in which a substrate for one of the enzymes is attached to an insoluble polymeric support material such as cellulose, and the mixture containing the enzyme is contacted with this insolubilised substrate. The enzyme becomes temporarily attached to the substrate, the support material is washed free of contaminants, and subsequently treated to recover the enzyme. This process works well in practice but suffers from the disadvantage that only a single enzyme can be removed from the mixture at any one time. As a consequence the separation of complex mixtures containing a number of enzymes can be a laborious and time consuming procedure.

It has now been found that certain groups of enzymes which require a co-enzyme for their reactivity can be readily separated from other organic materials and from one another, by taking advantage of their affinity for the co-enzyme and attaching the co-enzyme to an insoluble support.

The present invention comprises, as a new composition of matter, a reactive matrix comprising a co-enzyme chemically attached to a water insoluble organic polymeric support material.

Also, according to the invention, a process for the separation of mixtures containing a plurality of enzymes, comprises contacting the enzyme mixture in solution with a reactive matrix comprising an insoluble organic polymeric support material having chemically attached thereto a co-enzyme for the enzymes so that the enzymes become attached to the support, removing the support from the solution and eluting the enzyme sequentially from the support.

The binding between an enzyme and its co-enzyme is usually very weak compared to a covalent bond, and yet surprisingly it is sufficient to allow separation by the process of the invention. An outstanding feature of the invention is that it can permit the strength of the enzyme-co-enzyme binding to be altered, for example, by contacting the reactive matrix with the enzymes attached thereto with a solution of a small molecule such as a substrate or inhibitor for one or more of the enzymes or even potassium chloride, so that the enzymes can be eluted in a desired order. It has also been found that it is desirable to contact the enzyme mixture with the reactive matrix in the presence of a substrate for at least one of the enzymes to be separated. In a preferred method of operation the enzyme mixture, dissolved in a solution of a suitable buffer salt such as an inorganic phosphate is contacted with the reactive matrix. the matrix is then washed with a solution of the buffer containing a quantity of a substrate for at least one of the enzymes and the mixture of enzymes is separated from the matrix by elution with solutions of increasing ionic concentration or by elution with solutions of components of the enzyme reaction e.g. NAD or NADH.

Enzymes which may be separated and purified by the process of the invention include crude enzymes, enzyme mixtures and enzyme systems present in or isolated from animal, plant, or micro biological tissues and crude extracts of these tissues and synthetic enzymes such as those prepared by the solid phase method of Merrifield. Examples of groups of enzymes whose activity depends on the presence of a co-enzyme include dehydrogenases such as alcohol dehydrogenase, lactate dehydrogenase, and threonine dehydrogenase, oxidases such as d- and l- amino acid oxidase, decarboxylases such as lysine decarboxylase and arginine decarboxylase and kinases such as hexokinase and glucokinase.

The insoluble organic polymeric support material can comprise a natural or synthetic polymeric material, particularly a hydrophilic material such as for example a polyacrylamide or a polymer having free hydroxyl groups such as cellulose, cellulose derivatives, starch, dextran and cross-linked dextrans for example "Sephadex" (Trade Mark) Sepharose (TM), proteins such as wool, and polyvinyl alcohol. Other polymeric materials which can be used include nylon, polyesters, such as polyethylene terephthalate, cellulose acetate, and substituted cross-linked polystyrenes such as chloromethylated polystyrenes.

The polymeric material may take the form of beads, or a sheet of fabric for example a woven fabric or any other convenient cast or extruded shape. Preferably it is produced in the form of a permeable material which is adapted to make up a packed column.

The co-enzyme that is chemically attached to the polymeric material can be, for example, nicotinamide adenine dinucleotide (NAD), nicotinamide adenine dinucleotide phosphate (NADP) and their reduced forms, adenosine diphosphate ribose (ADP-Ribose), adenosine triphosphate (ATP), adenosine diphosphate (ADP), adenosine monophosphate (AMP). pyridoxamine phosphate, pyridoxal phosphate, and pterins.

The co-enzymes may be attached to the polymeric material by a variety of chemical techniques. Azide gorups or chloro s-triazinyl groups may be formed on the polymeric matrix which will react directly with the co-enzyme without affecting its ability to attach itself to an enzyme molecule. In a particularly preferred technique, cellulose, a cellulose derivative, or another polymeric material containing a plurality of vicinal diol groups is treated with cyanogen bromide and then with the co-enzyme according to the following reaction scheme.

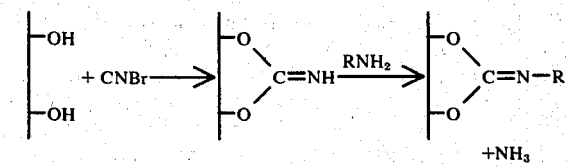

In the above reaction scheme RNH$_2$ represents the co-enzyme. Preferably the co-enzyme is linked to the backbone of the polymer chain by an intermediate carbon chain containing either 2 – 20 carbon atoms or oligopeptides or polyaromatic systems such as benzidine bridges.

The process of the invention is preferably carried out by flowing a solution of the enzyme mixture through a packed column of the reactive matrix. After washing the column to remove unwanted materials the enzymes attached thereto are removed sequentially by elution, preferably with buffered solutions of increasing ionic strength or buffered solutions of cofactors for the enzymes. It is found that different enzymes are removed from the column at different and characteristic ionic strengths thus affording a method of separating and purifying the enzymes. Inorganic phosphate buffer solutions and potassium chloride solutions have been found to be eminenty suitable as means for increasing the ionic strength.

Where the mixture contains only two enzymes an alternative and simpler procedure may be adopted. In the first stage the enzymes are attached to the reactive matrix as previously described and then washed with a solution of a substrate or effector for one of the enzymes. It is found that this technique often binds more tightly to the support the enzyme whose substrate or effector has been flowed through the column and removes the other enzyme in the eluent. The enzyme remaining on the support may be removed by washing with a buffer solution of higher ionic strength or by removal of the effector or by addition of a competitor for this effector.

The invention is illustrated by the following Examples:

EXAMPLE 1

This Example describes the separation of a mixture of L-malate dehydrogenase and L-lactate dehydrogenase on NAD-cellulose.

10 grams of cellulose powder are activated by the cyanogen bromide technique of Axen, Porath and Emback, Nature 1967 214 page 1302 and reacted with 100 milligrams of nicotinamide adenine dinucleotide in 0.1. molar sodium carbonate buffer pH 9 for 12 hours.

A synthetic mixture is made up of L-malate dehydrogenase (MDH). L-lactate dehydrogenase (LDH) and bovine serum albumin (BSA) and dialysed overnight against 10 millimolar phosphate buffer. The NAD-cellulose is packed into a column 5 mm in diameter and 20 mm in height and equilibrated with 10 millimolar phosphate buffer pH 7.5. A 50 microliter sample containing 0.335 units of MDH, 1.85 units of LDH and 0.8 mg of BSA is applied to the column and non-adsorbed protein washed off with 2 milliliters of phosphate buffer.

The column is then eluted with a potassium chloride gradient in 10 millimolar phosphate buffer, the gradient being from 0 to 0.5 molar KC1 (20 milliliters total), MDH, LDH and BSA are assayed in the effluent from the column, and the initial and final specific activities, recoveries and purification factors are given in the following Table:

| enzyme | units added | initial specific activity (units/mg) | units recovered | final specific activity (units/mg) | Purification (fold) |
|---|---|---|---|---|---|
| MDH | 0.335 | 0.42 | 0.3 | 20 | 47.6 |
| LDH | 1.85 | 2.30 | 1.3 | 26 | 11.3 |
| BSA | 0.8 mg | | | | |

It is found that MDH is eluted at 0.1 molar KCl, BSA at 0.175 molar KCl and LDH at 0.3 molar KCl.

EXAMPLE 2

This example illustrates the chromatography of a crude extract of *Pseudomonas oxalaticus* on NAD-cellulose prepared as described in Example 1. The crude extract was dialysed overnight against 10mM phosphate buffer pH 7.5 and a 0.5 ml sample applied to a 1.4 cm × 9.0 cm column of NAD-cellulose equilibrated with the same buffer. Non-absorbed protein was washed off the column with 40 ml of the buffer and enzyme eluted with a potassium phosphate gradient: 0.01 to 0.5M; 160 ml total volume, at a flow rate of 30 ml/hr. The following enzymes were assayed in the eluate and the concentration of phosphate required to elute them is given in parenthesis.

D-Glucose 6-Phosphate Dehydrogenase (45 mM)
L-Lactate Dehydrogenase (130 mM)
L-Threonine Dehydrogenase (c.250 mM)

A major inert protein peak was eluted at 45mM phosphate as shown in FIG. 1.

EXAMPLE 3

This example illustrates the chromatography of L-Threonine Dehydrogenase from a dialysed crude extract of *Pseudomonas oxalaticus* on NAD-cellulose in the absence (A) and presence (B) of 10mM L-Threonine. The procedure as in Example 2 was adopted except that in case B, 10 mM L-Threonine was included in the buffer and gradient.

Figure 2A:
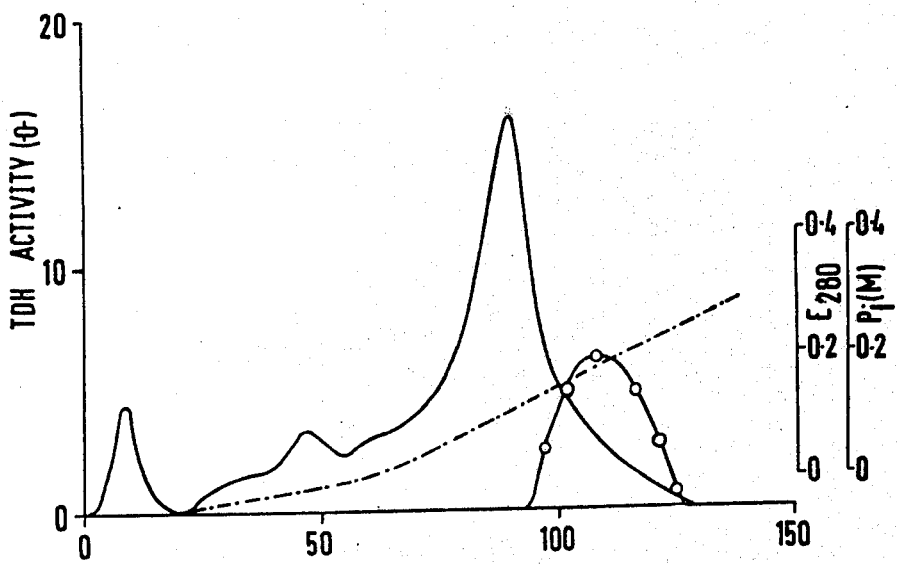
Figure 2B:
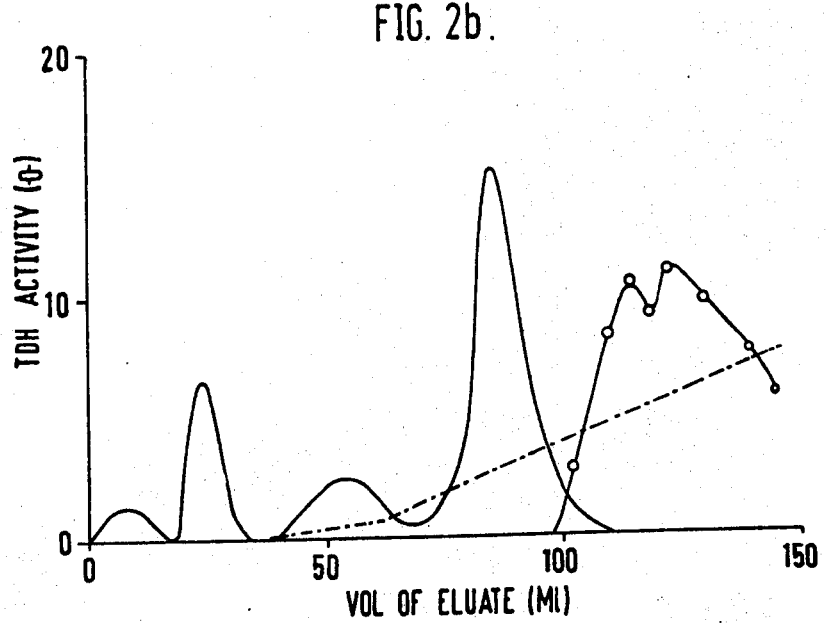

L-Threonine dehydrogenase and a major enzymically active protein peak was eluted at the following concentrations of potassium phosphate as shown in FIG. 2.

| | (A) No Threonine | (B) 10mM L-Threonine |
|---|---|---|
| L-Threonine Dehydrogenase | 220mM | 220mM |
| Inert Protein | 140mM | 90mM |

This example illustrates the advantage of including L-Threonine in the buffer system to assist in the purification of the enzyme L-Threonine Dehydrogenase on NAD-cellulose.

EXAMPLE 4

This example illustrates the affinity chromatography of L-Threonine Dehydrogenase from a crude extract of *Pseudomonas oxalaticus* on a diazo-linked NAD-cellulose derivative prpeared as follows. o-Amino-phenol was coupled to cellulose by the cyanogen bromide technique of Axen, Porath and Emback (1967). The o-hydroxyamino-cellulose (15g) was treated with diazotized benzidine (ex 1g Benzidine-HCl) at 0° C for 10 minutes. The cellulose derivative was washed with ice-cold water for 10 minutes and suspended in a solution of NAD (50 mg) in 0.1 molar sodium bicarbonate buffer, pH 9.0 (15 ml). The suspension was stirred overnight at 0° C and washed thoroughly with a large volume of ice-cold distilled water.

A 50 microliter sample of the crude dialysed extract was applied to a 5 mm × 20 mm column of the diazo-linked NAD-cellulose equilibrated with 10 mM phosphate buffer, pH 7.5. Non-absorbed protein was washed off with 10 ml of the same buffer and enzyme eluted with a potassium chloride gradient, 0 – 0.5 molar; 20 ml total volume at a flow rate of 5–6 ml/hr.

Figure 3:
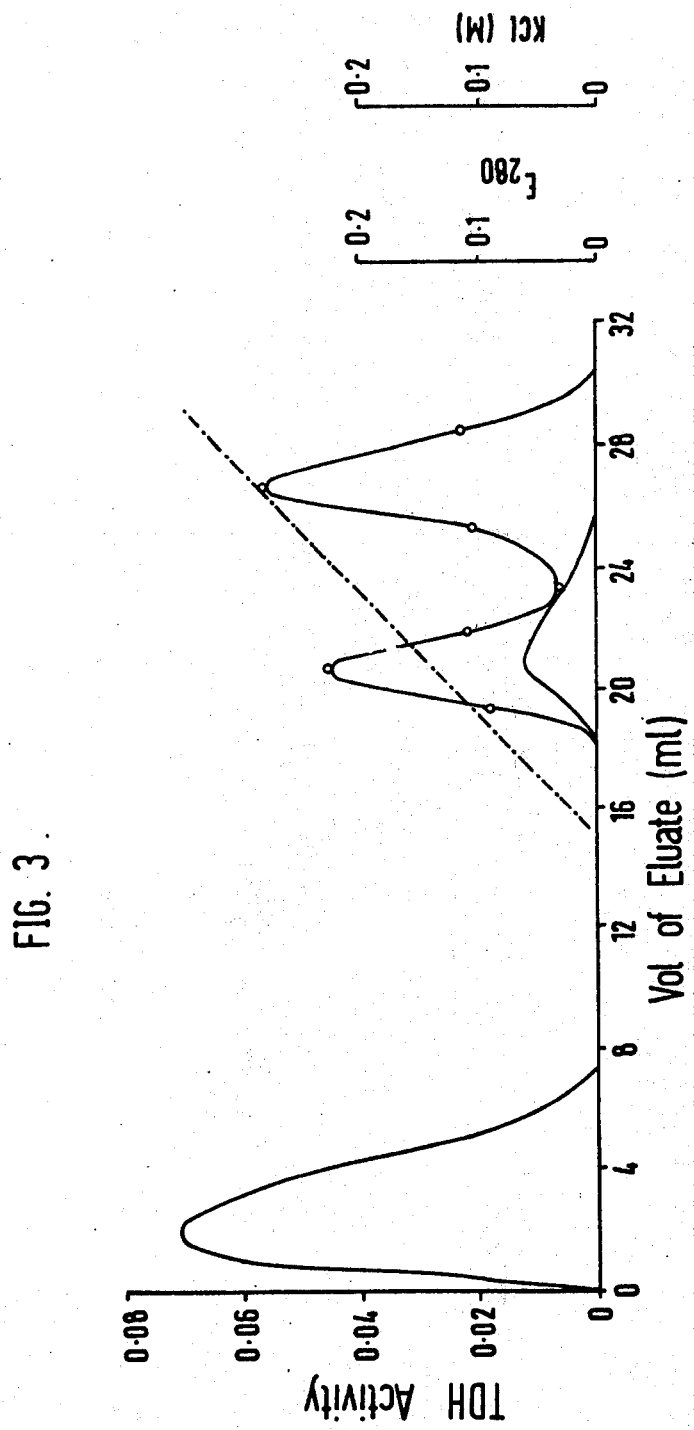

L-Threonine Dehydrogenase and other enzymically active protein were assayed in the effluent as shown in FIG. 3.

EXAMPLE 5

This example demonstrates the chromatography of D-Glucose 6-Phosphate Dehydrogenase from a crude yeast extract on $\epsilon$-Amino-caproyl-NADP-sepharose prepared as follows:

$\epsilon$-Amino-caproyl-sepharose was prepared by coupling $\epsilon$-Aminocaproic acid (1g) to sepharose 4B (10g) by the method of Axen, Porath and Emback (1967). To 10g of this polymer were added dicyclohexyl carbodiimide (5g) in Pyridine (12 ml) and NADP (100 mg) in water (3 ml). This mixture was rotated slowly for 10 days at room temperature and the gel washed successively with 80% aqueous pyridine, ethanol, butanol, ethanol, water, 2M KCl and finally water.

A sample (1 ml) of the crude yeast extract was applied to a 1 cm × 5cm column of $\epsilon$-Amino-caproyl-NADP-sepharose equilibrated with 0.05 molar triethanolamine-NaOH buffer, pH 7.6. Non-absorbed protein was washed off with 50 ml of the same buffer and enzyme eluted with a potassium chloride gradient, 0 – 0.5 molar, 200 ml total volume, at a flow rate of 12 ml/hr.

Figure 4:
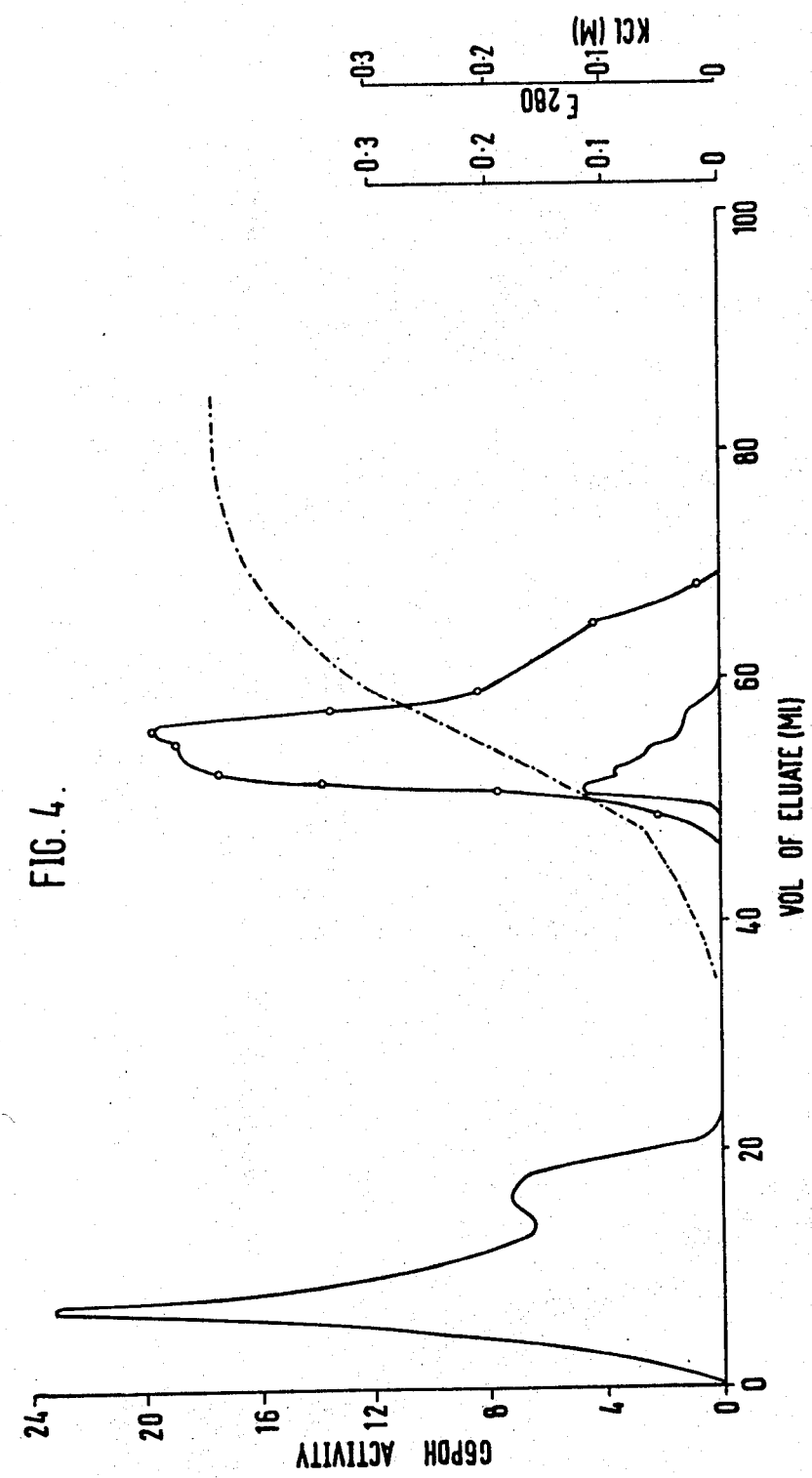

D-Glucose 6-Phosphate Dehydrogenase and other enzymically-active protein were assayed in the effluent. Enzyme was eluted at 0.15 KCl, its specific activity increasing from 0.29 $\mu$moles NADPH/min/mg in the initial extract to 6.50 $\mu$moles NADPH/min in the purified product as shown in FIG. 4. Recovery of enzyme activity was quantitative.

EXAMPLE 6

This example illustrates the isolation of $\beta$-Hydroxybutyrate Dehydrogenase from a crude extract of *Rhodopseudomonas sphaeroides* on $\epsilon$-Amino-caproyl-NAD-sepharose. The reactive matrix was prepared as described in example 5 except that NAD was used in place of NADP.

Figure 5:
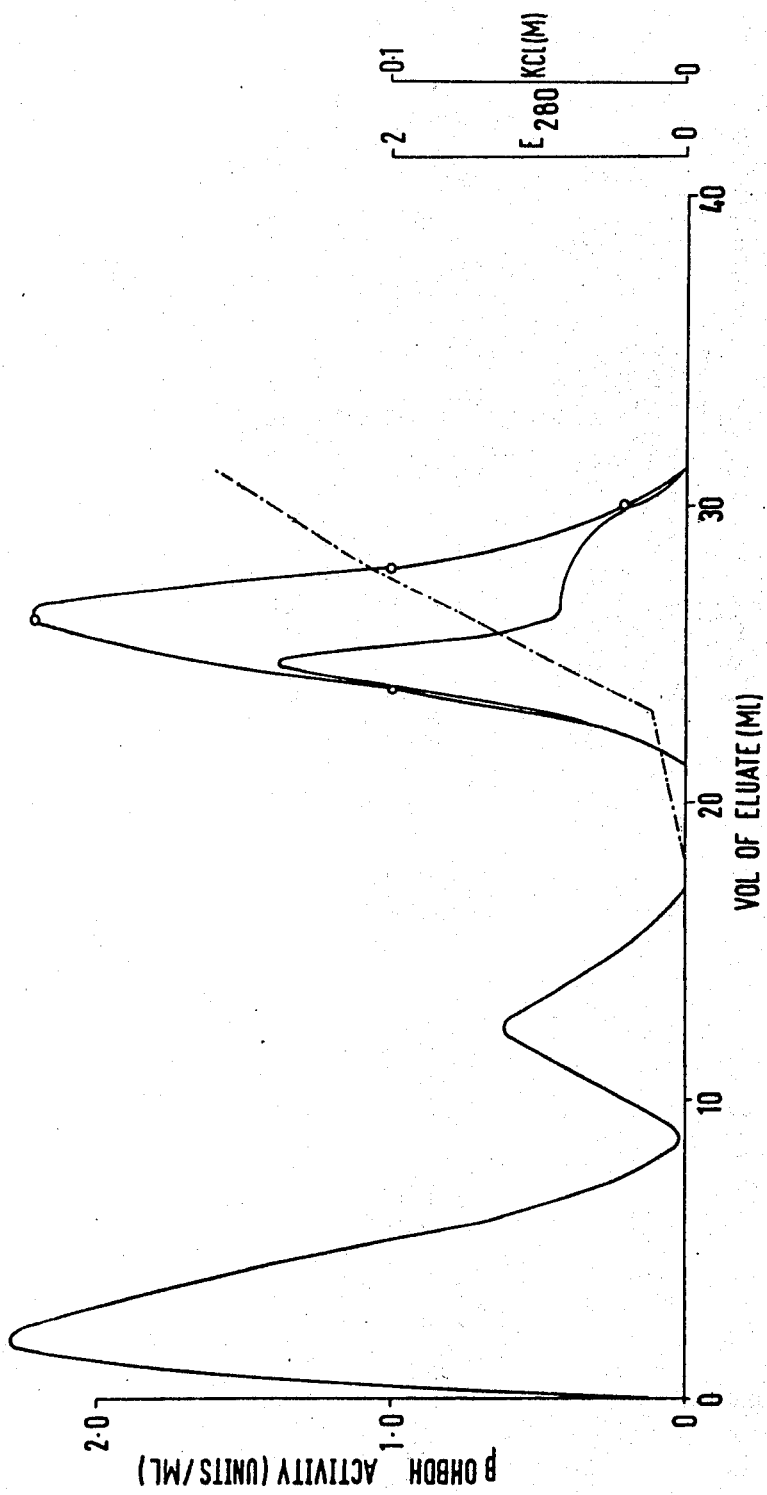

A 50 microliter sample of the crude extract was applied to a 5 mm × 20 mm column of $\epsilon$-Amino-caproyl-NAD-sepharose equilibrated with 0.05 molar Tris-HCl buffer, pH 8.0. Non-absorbed protein was washed off with 20 ml of the same buffer, and enzyme eluted with a gradient of potassium chloride, 0 to 0.5 molar in 0.05 molar Tris-HCl buffer, pH 8.0. The specific activity of the $\beta$-Hydroxy-Butyrate Dehydrogenase increased from $3.1 \times 10^{-4}$ $\mu$moles NADH formed/min/mg protein to approximately $3 \times 10^{-2}$ $\mu$moles NADH/min/mg, as shown in FIG. 5 an increase of some 100-fold.

EXAMPLE 7

This example summarises in table form some results obtained with differing coenzymes, matrices, enzymes and extension 'arms'. The results are expressed terms of the concentration of potassium chloride required to elute the enzyme or bovine serum albumin in synthetically prepared mixtures. The procedure described in example 1 was used in each case.

EXAMPLE 7

| Matrix | Coenzyme | Extension 'Arm' | Enzyme | Salt Concentration Reqd. to elute Enzyme | BSA | Comments |
|---|---|---|---|---|---|---|
| Cellulose | ADP | None | L-Lactate Dehydrogenase | 280 | 155 | |
| Cellulose | ADP-Ribose | None | L-Lactate Dehydrogenase | 295 | 140 | |
| Cellulose | ADP-Ribose | None | L-Glutamate Dehydrogenase | 460 | 155 | |
| Sephadex G-200 | NAD | None | L-Lactate Dehydrogenase | 120 | 0 | |
| Sephadex G-100 | NAD | None | L-Malate Dehydrogenase | 90 | 0 | |
| Sepharose | AMP | $\epsilon$-Amino-caproyl | L-Malate Dehydrogenase | 90 | 0 | |
| Sepharose | AMP | $\epsilon$-Amino-caproyl | Isocitrate Dehydrogenase | 190 | 0 | |
| " | NAD | $\epsilon$-Amino-caproyl | Glyceraldehyde 3-Phosphate Dehydrogenase | >1000 | 0 | Enzyme eluted with a 200 microlitre pulse of 5mM NADH |
| " | NAD | Triglycyl | L-Lactate Dehydrogenase | 85 | 0 | Enzyme eluted with 50 mM NAD |
| " | NAD | $\epsilon$-Amino-caproyl | L-Lactate Dehydrogenase | >1000 | 0 | Column equilibrated with 5mM $Na_2SO_3$ in all buffers: enzyme eluted with 5mM NADH |
| " | NADP | $\epsilon$-Amino-caproyl | D-Glucose 6-Phospate Dehydrogenase | 125 | 0 | |

We claim:

1. A reactive matrix consisting essentially of a coenzyme chemically attached to a water-insoluble organic polymeric support material in which the coenzyme is nicotinamide adenine dinucleotide, said reactive matrix being free from chemically attached enzymes, said water-insoluble organic polymeric support material containing said co-enzyme chemically attached thereto being capable of attracting enzymes in affinity chromatography which are attracted to said coenzyme, thereby making it possible to separate enzymes from other components of a liquid medium containing said enzymes as well as other enzymes.

2. A matrix according to claim 1, in which the organic polymeric support material is hydrophilic.

3. A matrix according to claim 1, in which the organic polymeric support material is in the form of a permeable material which is adapted to make up a packed column.

4. A matrix according to claim 1, in which the organic polymeric support material is a polymer containing a plurality of vicinal diol groups which have been reacted with cyanogen bromide.

5. A matrix according to claim 1, in which the coenzyme is linked to the backbone of the polymer chain of the organic polymeric support material by an intermediate carbon chain containing from 2 to 20 carbon atoms or by an oligopeptide or a polyaromatic system.

6. A matrix according to claim 1, in which the organic polymeric support material is polyacrylamide.

7. A matrix according to claim 1, in which the organic polymeric support material is selected from the group consisting of polyacrylamide, cellulose acetate, a starch, a dextran, a protein, polyvinyl alcohol, nylon, a polyester, chloromethylated polystyrenes and polymers containing a plurality of vicinal diol groups which have been reacted with cyanogen bromide.

8. A matrix according to claim 4, in which said polymer is cellulose.

* * * * *